US011352318B2

(12) United States Patent
Iida et al.

(10) Patent No.: US 11,352,318 B2
(45) Date of Patent: Jun. 7, 2022

(54) PRODUCTION METHOD FOR DICYANOCYCLOHEXANE

(71) Applicant: Mitsubishi Gas Chemical Company, Inc., Chiyoda-ku (JP)

(72) Inventors: Akifumi Iida, Niigata (JP); Emi Nakano, Niigata (JP); Yutaka Kanbara, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 75 days.

(21) Appl. No.: 16/636,182

(22) PCT Filed: Aug. 6, 2018

(86) PCT No.: PCT/JP2018/029396
§ 371 (c)(1),
(2) Date: Feb. 3, 2020

(87) PCT Pub. No.: WO2019/035381
PCT Pub. Date: Feb. 21, 2019

(65) Prior Publication Data
US 2020/0165195 A1 May 28, 2020

(30) Foreign Application Priority Data

Aug. 18, 2017 (JP) .............................. JP2017-158153

(51) Int. Cl.
*C07C 253/22* (2006.01)
*C07C 209/48* (2006.01)
(52) U.S. Cl.
CPC .......... *C07C 253/22* (2013.01); *C07C 209/48* (2013.01)
(58) Field of Classification Search
CPC ............................ C07C 253/22; C07C 209/48

USPC ......................................................... 558/313
See application file for complete search history.

(56) References Cited

U.S. PATENT DOCUMENTS

| 8,865,938 B2 | 10/2014 | Yoshimura et al. |
| 2013/0197269 A1 | 8/2013 | Yoshimura et al. |
| 2013/0197270 A1 | 8/2013 | Yoshimura et al. |
| 2016/0207875 A1 | 7/2016 | Fukuda et al. |
| 2019/0225572 A1 | 7/2019 | Iida et al. |

FOREIGN PATENT DOCUMENTS

| CN | 105016944 A | 11/2015 |
| EP | 2 626 343 A1 | 8/2013 |
| EP | 2 626 344 A1 | 8/2013 |
| JP | 5562429 B2 | 7/2014 |
| JP | 5640093 B2 | 12/2014 |
| WO | WO 2012/046781 A1 | 4/2012 |
| WO | WO 2012/046782 A1 | 4/2012 |
| WO | WO 2015/016148 A1 | 2/2015 |
| WO | WO 2018/066447 A1 | 4/2018 |

OTHER PUBLICATIONS

International Search Report dated Sep. 11, 2018 in PCT/JP2018/029396 filed Aug. 6, 2018, citing documents AB-AD and AQ-AU therein, 2 pages.

*Primary Examiner* — Kristin A Vajda
(74) *Attorney, Agent, or Firm* — Oblon, McClelland, Maier & Neustadt, L.L.P.

(57) ABSTRACT

The present invention provides a production method for dicyanocyclohexane, including a step of obtaining dicyanocyclohexane by reacting cyclohexanedicarboxylic acid and/or a salt thereof, or a heated concentrate of an aqueous ammonia solution of cyclohexanedicarboxylic acid with ammonia in a solvent having a boiling point equal to or higher than a reaction temperature.

16 Claims, No Drawings

PRODUCTION METHOD FOR DICYANOCYCLOHEXANE

TECHNICAL FIELD

The present invention relates to a production method for dicyanocyclohexane.

BACKGROUND ART

Bis(aminomethyl)cyclohexane is an industrially important compound, which is used as a raw material for an epoxy curing agent, polyamide, polyurethane, etc. Therefore, a method of producing bis(aminomethyl)cyclohexane has been examined.

For example, Patent Literatures 1 and 2 disclose obtaining bis(aminomethyl)cyclohexane by a hydrogenation reaction of dicyanocyclohexane. It has also been demanded to obtain this dicyanocyclohexane efficiently because it is an important intermediate for synthesizing bis(aminomethyl)cyclohexane.

Patent Literatures 1 and 2 disclose that dicyanocyclohexane is produced by nucleus-hydrogenating at least one of terephthalic acid or a derivative thereof selected from the group consisting of terephthalic acid, terephthalic acid ester and terephthalamide, and bringing the obtained hydrogenated terephthalic acid or a derivative thereof, that is, cyclohexanedicarboxylic acid or a derivative thereof into contact with ammonia for cyanation. Upon this, the reaction temperature of cyanation is 280° C., and the cyanation is carried out in a solvent such as N,N-dimethylimidazolidinone (boiling point: 226° C.) or ethylene glycol dimethyl ether (boiling point: 275° C.)

CITATION LIST

Patent Literature

Patent Literature 1

Japanese Patent No. 5640093

Patent Literature 2

Japanese Patent No. 5562429

SUMMARY OF INVENTION

Technical Problem

When cyclohexanedicarboxylic acid is brought into contact with ammonia for the cyanation reaction, impurities are generated. Examples of the impurity may include a by-product generated by a further reaction of dicyanocyclohexane, which is a product of the cyanation reaction, and specific examples thereof include a trimer of dicyanocyclohexane. Generation of such a by-product may lead to a decrease in the yield of dicyanocyclohexane, which is the target compound, or may bring about a need to remove such a by-product from the product. Therefore, it has been demanded to suppress generation of a by-product from the viewpoint of efficiently obtaining dicyanocyclohexane.

An object of the present invention is to provide a production method for dicyanocyclohexane by which dicyanocyclohexane is obtained with a high yield and generation of impurities can be suppressed.

Solution to Problem

The present inventors have, as a result of devoted studies to solve the above problem, found out that, when the cyanation reaction of cyclohexanedicarboxylic acid is carried out in a solvent having a boiling point higher than the reaction temperature of cyanation, dicyanocyclohexane is obtained with a high yield and generation of impurities can be suppressed.

More specifically, the present invention is as follows.

[1]

A production method for dicyanocyclohexane, comprising a step of obtaining dicyanocyclohexane by reacting cyclohexanedicarboxylic acid and/or a salt thereof, or a heated concentrate of an aqueous ammonia solution of cyclohexanedicarboxylic acid with ammonia in a solvent having a boiling point equal to or higher than a reaction temperature.

[2]

The production method for dicyanocyclohexane according to [1], further comprising a step of obtaining the cyclohexanedicarboxylic acid and/or the salt thereof, or the aqueous ammonia solution of cyclohexanedicarboxylic acid by a hydrogenation reaction of phthalic acid in an aqueous ammonia solution.

[3]

The production method for dicyanocyclohexane according to [1] or [2], wherein a part of an aqueous ammonia solution included in a reaction solution after the step of obtaining the cyclohexanedicarboxylic acid and/or the salt thereof, or the aqueous ammonia solution of cyclohexanedicarboxylic acid is used as an ammonia source for the step of obtaining dicyanocyclohexane.

[4]

The production method for dicyanocyclohexane according to any of [1] to [3], further comprising a step of obtaining the heated concentrate by heating the aqueous ammonia solution of cyclohexanedicarboxylic acid to 100 to 200° C. to remove at least a part of water.

[5]

The production method for dicyanocyclohexane according to any of [1] to [4], wherein the solvent having the boiling point equal to or higher than the reaction temperature is one or more selected from the group consisting of alkylnaphthalene, stearic acid amide, stearonitrile and triphenylmethane.

[6]

A production method for bis(aminomethyl)cyclohexane, comprising a step of obtaining dicyanocyclohexane by the production method for dicyanocyclohexane according to any of [1] to [5], and then further obtaining bis(aminomethyl)cyclohexane by subjecting the dicyanocyclohexane to a hydrogenation reaction.

Advantageous Effects of Invention

The present invention can provide a production method for dicyanocyclohexane by which dicyanocyclohexane is obtained with a high yield and generation of impurities can be suppressed.

DESCRIPTION OF EMBODIMENT

Hereinafter, embodiments of the present invention (hereinafter, also referred to as the "present embodiment") will be described in detail. Note that the present invention is not limited to the present embodiment and can be conducted with various modifications without departing from the spirit thereof.

A production method for dicyanocyclohexane according to the present embodiment comprises a step of obtaining dicyanocyclohexane by reacting cyclohexanedicarboxylic acid and/or a salt thereof, or a heated concentrate of an aqueous ammonia solution of cyclohexanedicarboxylic acid with ammonia in a solvent having a boiling point equal to or higher than a reaction temperature (hereinafter, also simply referred to as the "cyanation step").

In cyclohexanedicarboxylic acid used for the production method according to the present embodiment, positions of carboxylic acid groups on the cyclohexane ring are not particularly limited. Specific examples of cyclohexanedicarboxylic acid include 1,2-cyclohexanedicarboxylic acid, 1,3-cyclohexanedicarboxylic acid and 1,4-cyclohexanedicarboxylic acid. Among them, 1,4-cyclohexanedicarboxylic acid is preferable.

In addition, cyclohexanedicarboxylic acid in the present embodiment may be a cis isomer, or a trans isomer, or a mixture of the cis isomer and the trans isomer.

Furthermore, cyclohexanedicarboxylic acid in the present embodiment includes its salt form. In the present specification, cyclohexanedicarboxylic acid includes its salt form, and thus, "cyclohexanedicarboxylic acid and/or a salt thereof" may also be simply described as "cyclohexanedicarboxylic acid."

Examples of the salt of cyclohexanedicarboxylic acid include salts of alkali metals such as sodium and potassium, and ammonium salt. These salts may be alone, or may be a mixture of two or more. In addition, ammonium salt of cyclohexanedicarboxylic acid is preferable as the salt of cyclohexanedicarboxylic acid.

In the production method for dicyanocyclohexane according to the present embodiment, as a raw material, cyclohexanedicarboxylic acid and/or a salt thereof may be used, or a heated concentrate of an aqueous ammonia solution of cyclohexanedicarboxylic acid may be used.

Cyclohexanedicarboxylic acid used as a raw material in the cyanation step may be produced according to an ordinary method for use, or may be commercially obtained for use.

When cyclohexanedicarboxylic acid is produced, it is preferable that cyclohexanedicarboxylic acid be obtained by subjecting phthalic acid in an aqueous ammonia solution to a hydrogenation reaction. That is, it is preferable that the production method for dicyanocyclohexane according to the present embodiment include a step (hereinafter, also simply referred to as a "nucleus hydrogenation step") of obtaining cyclohexanedicarboxylic acid or an aqueous ammonia solution of cyclohexanedicarboxylic acid by subjecting phthalic acid in an aqueous ammonia solution to a hydrogenation reaction (hereinafter, also simply referred to as a "nucleus hydrogenation reaction").

In addition, phthalic acid may be one selected from the group consisting of ortho isomer, meta isomer and para isomer, or may be a mixture of two or more. Phthalic acid is preferably a para isomer, that is, terephthalic acid.

When the production method for dicyanocyclohexane comprises the nucleus hydrogenation step, at least a part of an aqueous ammonia solution included in a reaction solution after this step can be used as ammonia, which is necessary for the cyanation step. Accordingly, the effective utilization of ammonia is also enabled.

In the nucleus hydrogenation step, for example, a catalyst and water are placed in a reactor at first; hydrogen gas is then introduced into the reactor until reaching a predetermined pressure; the suspension is heated and stirred while maintaining the pressure; and the catalyst is reduced to be activated.

For the catalyst, for example, catalysts used for a normal nucleus hydrogenation reaction can be employed. Examples of the catalyst include catalyst including a metal, preferably a noble metal. Specific examples of the above metal include at least one selected from the group consisting of Ru, Pd, Pt, Rh and the like.

The catalyst may be those in which the above metal as an active component is supported on a support. Examples of the above support include at least one selected from the group consisting of carbon, $Al_2O_3$, $SiO_2$, $SiO_2$—$Al_2O_3$, $TiO_2$, $ZrO_2$ and the like. When a support is used, the amount of the metal supported, which is an active component, is preferably 0.1 to 10% by mass with respect to 100% by mass of the support.

The reaction can be carried out in a slurry bed reactor or in a fixed bed reactor. For the reaction system, any of a batch system, semi-batch system and continuous system can be selected.

In addition, the pressure in the system upon the activation of the catalyst may be an ordinary pressure (the gas phase part is purged with hydrogen) or may be a positive pressure. The pressure in the system in the case where the system is pressurized to a positive pressure is preferably 0.1 to 8 MPa. Hydrogen gas may be introduced into the reactor appropriately in order to maintain a positive pressure. Furthermore, the activation temperature is preferably 50 to 250° C. By making conditions upon the activation of the catalyst within the ranges described above, the catalyst can be activated further more effectively and reliably. In addition, the stirring time may be any length as long as it is sufficient for activating the catalyst.

Next, the reactor is cooled and the hydrogen gas remaining in the system is discharged to outside the system; phthalic acid and an aqueous ammonia solution are then placed in the reactor; and furthermore, hydrogen gas is introduced until reaching a predetermined pressure. Upon this, the amount of the phthalic acid placed is preferably 2 to 20% by mass with respect to the entire reaction solution. In addition, the amount of the aqueous ammonia solution placed is preferably an amount that provides 200 to 400 mol % of ammonia with respect to 100 mol % of phthalic acid. There is no limitation on the amount of the catalyst used, and it may be appropriately determined to achieve the target reaction time, considering the content of the supported metal catalyst and the amount of phthalic acid used for the reaction. By using each raw material, etc. in an amount within the ranges described above, the yield of the obtained cyclohexanedicarboxylic acid can be enhanced.

Next, the inside of the reactor is heated to a predetermined temperature to make the nucleus hydrogenation reaction progress. The reaction temperature upon this is preferably 40 to 150° C. The reaction pressure is preferably 0.5 to 15 MPa in terms of the partial pressure of hydrogen. Note that the reaction time may be any length as long as it is long enough for the nucleus hydrogenation reaction to progress sufficiently. By adjusting the reaction conditions to be within the ranges mentioned above, the yield and selectivity of the obtained cyclohexanedicarboxylic acid can be enhanced. In addition, hydrogen gas may be appropriately introduced into the reactor in order to maintain the reaction pressure within the range described above.

When cyclohexanedicarboxylic acid is produced in a manner mentioned above, the reaction solution includes an aqueous ammonia solution and the produced ammonium salt of cyclohexanedicarboxylic acid. The production method according to the present embodiment can use at least a part of the aqueous ammonia solution as ammonia, which is necessary for the cyanation step, along with cyclohexanedicarboxylic acid produced in the nucleus hydrogenation step. By doing this, the effective utilization of ammonia is enabled. Among the ammonia in the reaction solution after the nucleus hydrogenation step, preferably 5 to 25% by mass of the ammonia can be used in the cyanation step.

In addition, the reaction solution after the nucleus hydrogenation step may be used as a raw material solution for the cyanation step, without collecting cyclohexanedicarboxylic acid by filtration or the like from the reaction solution after the nucleus hydrogenation step. By omitting a filtration step, the time from the nucleus hydrogenation step to the cyanation step can be shortened, which enables reduction of labor and costs.

It is preferable for the production method according to the present embodiment to have, prior to the cyanation step, a step (hereinafter, also simply referred to as a "heat concentration step") of obtaining the heated concentrate described above by heating the aqueous ammonia solution of cyclohexanedicarboxylic acid (that is, the aqueous ammonia solution including cyclohexanedicarboxylic acid) to remove at least a part of water.

In the heat concentration step, the amount of ammonia is preferably 100 moles to 200 moles with respect to 100 moles of cyclohexanedicarboxylic acid. In addition, in the heat concentration step, the concentration of ammonia in the initial aqueous ammonia solution is preferably 0.1 to 10% by mass with respect to the whole amount of the aqueous ammonia solution.

Furthermore, the heating temperature upon obtaining the heated concentrate is preferably 70° C. to 200° C. The pressure upon obtaining the heated concentrate may be a negative pressure, an ordinary pressure or a positive pressure.

By adjusting the concentration of each component and/or heating conditions to be within the ranges described above, the yield of dicyanocyclohexane in the cyanation step tends to be further increased. Particularly, the heating temperature within a range of 100° C. to 200° C. is preferred from the viewpoint of producing the heated concentrate by removing water via volatilization from the aqueous ammonia solution. In addition, in the present embodiment, the use of the heated concentrate described above for the cyanation step is useful in that ammonia present in the heated concentrate can be used effectively as a raw material for the cyanation reaction.

The heat concentration step may be performed sequentially with the subsequent cyanation step. The heated concentrate may be liquid or solid.

That is, an aqueous ammonia solution of cyclohexanedicarboxylic acid and water as necessary are placed in a reactor at first; and an inert gas is introduced until the pressure in the system reaches a predetermined pressure, optionally along with ammonia gas as necessary. Then, in order to maintain the pressure in the reactor within a constant range while retaining the temperature in the reactor within a range of preferably 100° C. to 200° C., the inert gas is introduced into the reactor or the gas in the reactor is discharged, appropriately, thereby obtaining a heated concentrate. The heated concentrate here may be isolated as a solid by carrying out a treatment such as filtration, and such a solid may be subjected to a step of drying water contained in the solid as necessary.

Next, the cyanation reaction may be carried out by introducing a catalyst, a solvent having a boiling point equal to or higher than the reaction temperature, and ammonia gas into the reactor that contains the heated concentrate, and adjusting the temperature and pressure in the reactor to be a temperature and pressure required for the cyanation step. In this case, it is preferable to introduce ammonia gas after obtaining the heated concentrate because by doing this, ammonia can be utilized more efficiently. Examples of the inert gas described above include nitrogen gas, as well as noble gases such as argon and helium. However, the inert gas does not have to be introduced into the system.

In the cyanation step, cyclohexanedicarboxylic acid or the heated concentrate of the aqueous ammonia solution of cyclohexanedicarboxylic acid, a solvent having a boiling point equal to or higher than the reaction temperature, water as necessary, and a catalyst are placed in a reactor at first; and an inert gas, appropriately along with ammonia gas, is introduced until the pressure in the system reaches a predetermined pressure. The predetermined pressure in the system after introducing the inert gas and ammonia gas may be a negative pressure, an ordinary pressure or a positive pressure. Then, the inside of the reactor is heated to a predetermined temperature, and the inert gas is appropriately introduced into the reactor in order to maintain the pressure in the reactor within a constant range while stirring the inside of the reactor, thereby making the cyanation reaction progress.

In the production method according to the present embodiment, when cyclohexanedicarboxylic acid is used as a reactant, cyclohexanedicarboxylic acid is brought into contact with ammonia by introducing ammonia into a reactor.

Examples of the method of introducing ammonia may include a method of adding an aqueous ammonia solution and a method of introducing ammonia gas. These methods may be used alone or used in combination.

In addition, when ammonia gas is introduced into a reactor, its flow rate may be appropriately adjusted according to the scale of reaction and the like, and normally, it is 0.1 to 5 moles per hour, preferably 0.3 to 4 moles per hour, and more preferably 0.5 to 3 moles per hour with respect to 1 mole of cyclohexanedicarboxylic acid.

In the production method according to the present embodiment, when a heated concentrate of an aqueous ammonia solution of cyclohexanedicarboxylic acid is used as a reactant, ammonia is already present in a reactor. However, it is preferable to further introduce ammonia from the viewpoint of making the reaction into dicyanocyclohexane progress sufficiently.

Examples of the method of introducing ammonia may include a method of adding an aqueous ammonia solution and a method of introducing ammonia gas. These methods may be used alone or used in combination.

In addition, when ammonia gas is introduced into a reactor, its flow rate may be appropriately adjusted according to the scale of reaction and the like, and normally, it is 0.1 to 5 moles per hour, preferably 0.3 to 4 moles per hour, and more preferably 0.5 to 3 moles per hour with respect to 1 mole of cyclohexanedicarboxylic acid contained in the heated concentrate of an aqueous ammonia solution of cyclohexanedicarboxylic acid.

When ammonia gas is introduced into a reactor, the amount of the ammonia gas used is preferably 200 to 1000 mol % with respect to 100 mol % of cyclohexanedicarboxylic acid. Accordingly, the yield of the obtained dicyanocyclohexane can be enhanced.

When an inert gas is introduced into a reactor, its flow rate may be appropriately adjusted according to the scale of reaction and the like, and normally, it is 0 to 50 L per hour, preferably 0 to 40 L per hour, and more preferably 0 to 30 L per hour with respect to 1 mole of cyclohexanedicarboxylic acid.

In the cyanation step, the concentration of cyclohexanedicarboxylic acid is preferably 50 to 1000 mol % with respect to 100 mol % of ammonia. In addition, in the cyanation step, the concentration of ammonia in the aqueous ammonia solution is preferably 0.1 to 10% by mass with respect to the whole amount of the aqueous ammonia solution.

For the catalyst, either homogeneous catalyst or heterogeneous catalyst can be used.

For the catalyst, a catalyst used for an ordinary cyanation reaction can be employed, and more particularly, examples of the catalyst include metal oxides, such as silica gel, alumina, silica alumina, hydrotalcite, magnesium oxide, zinc oxide, tin oxide, iron oxide, titanium oxide, zirconium oxide, hafnium oxide, manganese oxide, tungsten oxide, vanadium pentoxide, niobium pentoxide, tantalum oxide, gallium oxide, indium oxide, and scandium oxide. These may be a simple substance, a complex oxide, or those supported on a support. Examples of the supported component include alkali metals such as sodium, lithium, potassium, rubidium and cesium, tin, rhenium, manganese, molybdenum, tungsten, vanadium, iron, nickel, chromium, boric acid, hydrochloric acid, and phosphoric acid.

In addition, examples of the catalyst also include rhenium compounds such as perrhenic acid and rhenium oxide, organic tin compounds such as dibutyltin oxide, ruthenium compounds such as dichlorotris(triphenylphosphine)ruthenium (II), and cobalt oxide.

Among these, zinc oxide and tin oxide are preferred from the viewpoint of making the cyanation reaction progress more effectively and reliably. These catalysts are used singly or in combinations of two or more. Furthermore, the amount of the catalyst used is preferably 0.1 to 20% by mass with respect to 100% by mass of cyclohexanedicarboxylic acid. By setting the amount of the catalyst within the range described above, the yield of the obtained dicyanocyclohexane can be enhanced.

The reaction temperature in the production method according to the present embodiment is not particularly limited as long as it is a temperature at which the cyanation reaction progresses, and it is preferably 270 to 400° C., more preferably 280° C. to 380° C., and further preferably 290° C. to 350° C.

The reaction pressure in the production method according to the present embodiment may be a negative pressure, an ordinary pressure or a positive pressure.

The reaction time may be any length as long as it is long enough for the cyanation reaction to progress sufficiently. By adjusting the concentration of each raw material and/or the reaction conditions to be within the ranges mentioned above, the yield of dicyanocyclohexane can be enhanced.

The solvent having a boiling point equal to or higher than a reaction temperature in the production method according to the present embodiment is a solvent having a boiling point equal to or higher than the reaction temperature in the cyanation step. Here, the reaction temperature in the cyanation step is a temperature from the reaction initiation time to the reaction termination time, and is preferably a temperature from the time of initiating heating for cyanation to the reaction termination time. In the present embodiment, by using a solvent having a boiling point equal to or higher than the reaction temperature, generation of impurities such as a trimer of dicyanocyclohexane can be suppressed, and dicyanocyclohexane with a high purity can be obtained.

In addition, by using a solvent having a boiling point equal to or higher than the reaction temperature, distillation of the solvent until reaching the reaction temperature in the cyanation step can be prevented, and costs for adding the solvent can be suppressed.

Furthermore, in the case where a solvent having a boiling point lower than the reaction temperature in the cyanation step is used, upon distilling off and purifying dicyanocyclohexane from the reaction mixture after the cyanation step, such a solvent needs to be distilled off in advance at a low temperature. Upon this, it is hard to completely remove the solvent having a low boiling point and the solvent tends to be contaminated into a fraction obtained by distilling off dicyanocyclohexane, thereby making the purification insufficient. Accordingly, by using the solvent having a boiling point equal to or higher than the reaction temperature, separation of dicyanocyclohexane and the solvent can be carried out readily.

The difference between the boiling point of the solvent and the reaction temperature is preferably 0° C. or more, more preferably 20° C. or more, and further preferably 50° C. or more. When the difference between the boiling point of the solvent and the reaction temperature is 0° C. or more, it is often possible to prevent the solvent from being distilled off until reaching the reaction temperature. In addition, when the difference between the boiling point of the solvent and the reaction temperature is 20° C. or more, upon the purification through distillation after the cyanation step, dicyanocyclohexane, which is the target compound, tends to be obtained with a high purity.

The upper limit of the difference between the boiling point of the solvent and the reaction temperature is not particularly limited, but it is normally 300° C. or less.

The boiling point of the solvent in the present embodiment is preferably 300° C. or higher, more preferably 320° C. or higher, and further preferably 350° C. or higher. When the boiling point is 300° C. or higher, the cyanation reaction progresses smoothly, and generation of impurities such as a trimer of dicyanocyclohexane can often be suppressed.

The upper limit of the boiling point is not particularly limited, but it is normally 600° C. or lower. The upper limit of the boiling point is preferably lower than 500° C., more preferably lower than 430° C., and further preferably lower than 420° C. from the viewpoint of further suppressing the generation of impurities such as a trimer of dicyanocyclohexane.

Specific examples of the solvent having a boiling point equal to or higher than the reaction temperature include: an aliphatic alkane such as heptadecane, nonadecane and docosane; an aliphatic alkene such as heptadecene, nonadecene and docosene; aliphatic alkyne such as heptadecyne, nonadecyne and docosyne; an alkyl-substituted aromatic such as alkylbenzene including undecylbenzene, tridecylbenzene and tetradecylbenzene, dialkylbenzene and alkylnaphthalene; an acid or acid anhydride such as 2,5-dichlorobenzoic acid and tetrachlorophthalic anhydride; an amide compound such as undecaneamide, lauric acid amide and stearic acid amide; a nitrile compound such as tetradecanenitrile, hexadecanenitrile, 2-naphthylacetonitrile and stearonitrile; a phosphorus compound such as p-chlorodiphenylphosphine and triphenyl phosphite; an amine such as 1,2-diphenylethylamine and trioctylamine; a hydroxide such as 2,2'-biphenol and triphenylmethanol; an ester such as benzyl benzoate and dioctyl phthalate; an ether such as 4-dibromophenyl ether; a halogenated benzene such as 1,2,4,5-tetrachloro-3-nitrobenzene and 4,4'-dichlorobenzophenone; a ketone such as 2-phenylacetophenone and anthraquinone; and triphenylmethane. These solvents are used singly or in combinations of two or more.

Here, the dialkylbenzene and alkylnaphthalene are aromatic hydrocarbon-based solvents containing one or two or more benzenes or naphthalenes having an alkyl group on the aromatic ring, and are commercially available.

Among the solvents described above, alkylnaphthalene, stearic acid amide, stearonitrile and triphenylmethane are preferable.

The solvent having a boiling point equal to or higher than the reaction temperature used in the present embodiment may be those in which a part of the solvent molecule is decomposed and/or converted in the cyanation step as long as it does not hinder progress of the cyanation reaction of cyclohexanedicarboxylic acid. There is no particular limitation on the solvent in which a part of the molecule is decomposed and/or converted as long as it does not hinder progress of the cyanation reaction before or after the decomposition or conversion, but the boiling point of the solvent after the decomposition or conversion is preferably equal to or higher than the reaction temperature.

Examples of the solvent that is to be decomposed and/or converted include stearic acid amide. Stearic acid amide may experience decomposition or conversion during the cyanation step and become stearonitrile. Stearonitrile has a boiling point of 274° C. at 13 kPa (boiling point at an ordinary pressure (converted value determined by pressure-temperature nomograph): 360° C.)), and thus, it is also suitable as the solvent in the cyanation step.

In the present specification, the "boiling point of a solvent" is a temperature at which the saturated vapor pressure of the liquid becomes equal to the external pressure.

The boiling point of the solvent used for the present embodiment may be a boiling point based on the information in The Merck Index (published by Royal Society of Chemistry), Material Safety Data Sheet (MSDS) and the like. If the boiling point is expressed with a certain width such as the range from the temperature of initiation point to the temperature of termination point of distillation, for example, due to the reason that such a solvent is composed of two or more components, the present embodiment employs the intermediate value between the temperature of initiation point and the temperature of termination point of distillation as the boiling point.

The amount used of the solvent having a boiling point equal to or higher than the reaction temperature is preferably 0.1 or more times, more preferably 0.5 or more times, further preferably 1.0 or more times, still further preferably 1.5 or more times, and even further preferably 2.0 or more times the mass of cyclohexanedicarboxylic acid. When the amount of the solvent used is 0.1 or more times the mass of cyclohexanedicarboxylic acid, the cyanation reaction progresses smoothly, and generation of impurities such as a trimer of dicyanocyclohexane can often be suppressed.

In addition, the amount used of the solvent having a boiling point equal to or higher than the reaction temperature is preferably 100 or less times, more preferably 30 or less times, and further preferably 10 or less times the mass of cyclohexanedicarboxylic acid. When the amount of the solvent used is 100 or less times the mass of cyclohexanedicarboxylic acid, dicyanocyclohexane can often be produced with a satisfactory energy efficiency.

Dicyanocyclohexane may be collected by distilling the reaction solution including dicyanocyclohexane thus obtained, as necessary (hereinafter, this step is referred to as a "distillation step"). Before the distillation, the catalyst may be separated, or deactivated or not deactivated. In addition, reactive distillation in which raw materials are supplied continuously and distillation is carried out along with the cyanation reaction can also be performed.

The distillation is performed by, for example, heating a distillation apparatus from the bottom section such that the pressure in the system in the distillation apparatus is 3.0 kPa to 4.0 kPa and the temperature is 180 to 230° C., and by cooling the top section, thereby performing gas-liquid contact in the apparatus. By doing this, dicyanocyclohexane can be selectively drawn and collected from the top section of the distillation apparatus.

In addition, in the present embodiment, dicyanocyclohexane, which is the target compound, can also be collected by methods other than distillation.

Specifically, if the reaction solution can be divided into two layers: a layer containing dicyanocyclohexane and a layer of the solvent, the layer containing dicyanocyclohexane and the layer of the solvent may be separated to collect dicyanocyclohexane. Examples of the solvent that forms two layers include an aliphatic alkane, alkylnaphthalene and alkylbenzene. The collection of dicyanocyclohexane utilizing separation of layers does not require heating or the like, and it is thus superior in energy efficiency.

A production method for bis(aminomethyl)cyclohexane according to the present embodiment comprises a step (hereinafter, also simply referred to as a "nitrile hydrogenation step") of obtaining bis(aminomethyl)cyclohexane by subjecting the obtained dicyanocyclohexane as mentioned above to a hydrogenation reaction (hereinafter, also referred to as a "nitrile hydrogenation reaction").

The nitrile hydrogenation reaction of bis(aminomethyl)cyclohexane can be carried out while referring to WO 2018/066447.

In the nitrile hydrogenation step, dicyanocyclohexane, a solvent, and a catalyst are placed in a reactor at first; and hydrogen gas is introduced until the pressure in the system reaches a predetermined pressure. Then, the inside of the reactor is heated to a predetermined temperature, and hydrogen gas is appropriately introduced into the reactor in order to maintain the pressure in the reactor within a constant range, thereby making the nitrile hydrogenation reaction progress.

For the solvent, a solvent used for an ordinary nitrile hydrogenation reaction can be employed, and more particularly, examples of the solvent include alcohols, such as methanol, ethanol, 1-propanol, 2-propanol, 1-butanol, 2-butanol and tert-butanol; aromatic hydrocarbons, such as meta-xylene, mesitylene and pseudocumene; and liquid ammonia. These solvents are used singly or in combinations of two or more. In addition, for the catalyst, for example, a catalyst used for an ordinary nitrile hydrogenation reaction can be employed, and more particularly, a catalyst containing Ni and/or Co can be used. Generally, for the catalyst, a catalyst made by supporting Ni and/or Co onto $Al_2O_3$, $SiO_2$, diatomaceous earth, $SiO_2$—$Al_2O_3$ or $ZrO_2$ by a precipitation method, Raney nickel, or Raney cobalt is suitably used. Among these, the Raney cobalt catalyst and Raney nickel catalyst are preferred from the viewpoint of making the nitrile hydrogenation reaction progress more effectively and reliably. These catalysts are used singly or in combinations of two or more. Furthermore, the amount of the catalyst used is preferably 0.1 to 150% by mass, more preferably 0.1 to 20% by mass, and further preferably 0.5 to 15% by mass with respect to 100% by mass of dicyanocyclohexane. By using the catalyst in an amount within the range described above, the yield and selectivity of the obtained bis(aminomethyl)cyclohexane can be enhanced.

The concentration of dicyanocyclohexane in the nitrile hydrogenation step is preferably 1 to 50% by mass and more preferably 2 to 40% by mass with respect to the whole amount of the reaction solution from the viewpoint of reaction efficiency. In addition, the reaction temperature in the nitrile hydrogenation step is preferably 40 to 150° C., and the reaction pressure is preferably 0.5 to 15 MPa in terms of the hydrogen partial pressure. Note that the reaction time may be any length as long as it is long enough for the nitrile hydrogenation reaction to progress sufficiently. By adjusting the reaction conditions to be within the ranges mentioned above, the yield and selectivity of the obtained bis(aminomethyl)cyclohexane can be enhanced.

EXAMPLES

Hereinafter, the present embodiment will be described in further detail based on Examples, but the present embodiment is not limited to the following Examples.

Example 1

In a 100 mL five neck flask equipped with a stirring blade, a gas introduction tube, a thermocouple and a dehydration apparatus, 10 g (0.06 mol) of 1,4-cyclohexanedicarboxylic acid (hereinafter, also described as 1,4-CHDA), 0.24 g of zinc oxide (manufactured by Kanto Chemical Co., Inc.) as a catalyst, and 20 g of alkylnaphthalene (BARREL process oil B-28AN manufactured by MATSUMURA OIL Co., Ltd., boiling point: 430° C.) as a solvent were placed. Then, heating was started, and nitrogen gas (flow rate: 20 NmL/min) and ammonia gas (flow rate: 52 NmL/min) were introduced at 170° C. After further elevating the temperature, bubbling in the reaction solution was started at 270° C., and the temperature was elevated to 300° C. The reaction solution was stirred at 300 rpm for 3.5 hours to carry out a cyanation reaction.

After the reaction finished, the reaction product was dissolved in tetrahydrofuran, and after further removing the catalyst in the solution by filtration, the reaction product was analyzed by gas chromatography (hereinafter, also described as GC) (model name "GC2010 PLUS" manufactured by Shimadzu Corporation, column: product name "HP-5 ms" manufactured by Agilent Technologies, 30 m length×0.25 mm i.d., film thickness 0.25 μm). As a result, the yield of 1,4-dicyanocyclohexane (hereinafter, also described as 1,4-CHDN) was 86.7 mol %.

Note that analytical conditions for GC were as follows.
Carrier gas: He (constant pressure: 73.9 kPa)
Inlet temperature: 300° C.
Detector: FID
Detector temperature: 300° C.
Column oven temperature: initially 100° C., elevated to 300° C. at 10° C./min, and retained at 300° C. for 30 mins)

Example 2

In a 100 mL five neck flask equipped with a stirring blade, a gas introduction tube, a thermocouple and a dehydration apparatus, 10 g (0.06 mol) of 1,4-cyclohexanedicarboxylic acid, 0.24 g of zinc oxide (manufactured by Kanto Chemical Co., Inc.) as a catalyst, and 20 g of stearic acid amide (manufactured by Tokyo Chemical Industry Co., Ltd., boiling point: 12 Torr, 250 to 251° C. (boiling point at an ordinary pressure (converted value determined by pressure-temperature nomograph): 410° C.)) as a solvent were placed. Then, heating was started, and nitrogen gas (flow rate: 20 NmL/min) and ammonia gas (flow rate: 52 NmL/min) were introduced at 170° C. After further elevating the temperature, bubbling in the reaction solution was started at 270° C., and the temperature was elevated to 300° C.

The reaction solution was stirred at 300 rpm for 3.5 hours to carry out a cyanation reaction.

After the reaction finished, the same operation as in Example 1 was carried out, and analysis by GC was carried out.

The yield of 1,4-dicyanocyclohexane was 89.2 mol %.

Example 3

In a 100 mL five neck flask equipped with a stirring blade, a gas introduction tube, a thermocouple and a dehydration apparatus, 10 g (0.06 mol) of 1,4-cyclohexanedicarboxylic acid, 0.24 g of zinc oxide (manufactured by Kanto Chemical Co., Inc.) as a catalyst, and 20 g of stearonitrile (manufactured by Tokyo Chemical Industry Co., Ltd., boiling point: 13 kPa, 274° C. (boiling point at an ordinary pressure (converted value determined by pressure-temperature nomograph): 360° C.)) as a solvent were placed. Then, heating was started, and nitrogen gas (flow rate: 20 NmL/min) and ammonia gas (flow rate: 52 NmL/min) were introduced at 170° C. After further elevating the temperature, bubbling in the reaction solution was started at 270° C., and the temperature was elevated to 300° C. The reaction solution was stirred at 300 rpm for 3.5 hours to carry out a cyanation reaction.

After the reaction finished, the same operation as in Example 1 was carried out, and analysis by GC was carried out.

The yield of 1,4-dicyanocyclohexane was 88.7 mol %.

Example 4

In a 100 mL five neck flask equipped with a stirring blade, a gas introduction tube, a thermocouple and a dehydration apparatus, 10 g (0.06 mol) of 1,4-cyclohexanedicarboxylic acid, 0.24 g of zinc oxide (manufactured by Kanto Chemical Co., Inc.) as a catalyst, and 20 g of triphenylmethane (manufactured by Wako Pure Chemical Industries, Ltd., boiling point: 359° C.) as a solvent were placed. Then, heating was started, and nitrogen gas (flow rate: 20 NmL/min) and ammonia gas (flow rate: 52 NmL/min) were introduced at 170° C. After further elevating the temperature, bubbling in the reaction solution was started at 270° C., and the temperature was elevated to 300° C. The reaction solution was stirred at 300 rpm for 3.5 hours to carry out a cyanation reaction.

After the reaction finished, the same operation as in Example 1 was carried out, and analysis by GC was carried out.

The yield of 1,4-dicyanocyclohexane was 91.5 mol %.

Example 5

In a 500 mL five neck flask equipped with a stirring blade, a gas introduction tube, a thermocouple and a dehydration apparatus, 100 g (0.58 mol) of 1,4-cyclohexanedicarboxylic acid, 0.80 g of zinc oxide (manufactured by Kanto Chemical Co., Inc.) as a catalyst, and 200 g of alkylnaphthalene (BARREL process oil B-28AN manufactured by MATSUMURA OIL Co., Ltd., boiling point: 430° C.) as a solvent were placed. Then, heating was started, and nitrogen gas (flow rate: 68 NmL/min) and ammonia gas (flow rate: 174 NmL/min) were introduced at 170° C. After further elevating the temperature, bubbling in the reaction solution was started at 270° C., and the temperature was elevated to 300° C. The reaction solution was stirred at 200 rpm for 8 hours to carry out a cyanation reaction.

After the reaction finished, the same operation as in Example 1 was carried out, and analysis by GC was carried out.

The yield of 1,4-dicyanocyclohexane was 92.0 mol %.

Example 6

In a 500 mL five neck flask equipped with a stirring blade, a gas introduction tube, a thermocouple and a dehydration apparatus, 100 g (0.58 mol) of 1,4-cyclohexanedicarboxylic acid, 0.80 g of zinc oxide (manufactured by Kanto Chemical Co., Inc.) as a catalyst, and 201 g of alkylnaphthalene (BARREL process oil B-28AN manufactured by MATSUMURA OIL Co., Ltd., boiling point: 430° C.) as a solvent were placed. Then, heating was started, and nitrogen gas (flow rate: 68 NmL/min) and ammonia gas (flow rate: 348 NmL/min) were introduced at 170° C. After further elevating the temperature, bubbling in the reaction solution was started at 270° C., and the temperature was elevated to 300° C. The reaction solution was stirred at 200 rpm for 5 hours to carry out a cyanation reaction.

After the reaction finished, the same operation as in Example 1 was carried out, and analysis by GC was carried out.

The yield of 1,4-dicyanocyclohexane was 89.0 mol %.

Example 7

In a 500 mL five neck flask equipped with a stirring blade, a gas introduction tube, a thermocouple and a dehydration apparatus, 50 g (0.29 mol) of 1,4-cyclohexanedicarboxylic acid, 0.40 g of zinc oxide (manufactured by Kanto Chemical Co., Inc.) as a catalyst, and 151 g of alkylnaphthalene (BARREL process oil B-28AN manufactured by MATSUMURA OIL Co., Ltd., boiling point: 430° C.) as a solvent were placed. Then, heating was started, and nitrogen gas (flow rate: 34 NmL/min) and ammonia gas (flow rate: 174 NmL/min) were introduced at 170° C. After further elevating the temperature, bubbling in the reaction solution was started at 270° C., and the temperature was elevated to 300° C. The reaction solution was stirred at 200 rpm for 8 hours to carry out a cyanation reaction.

After the reaction finished, the same operation as in Example 1 was carried out, and analysis by GC was carried out.

The yield of 1,4-dicyanocyclohexane was 94.3 mol %.

Example 8

In a 500 mL five neck flask equipped with a stirring blade, a gas introduction tube, a thermocouple and a dehydration apparatus, 100 g (0.58 mol) of 1,4-cyclohexanedicarboxylic acid, 0.80 g of zinc oxide (manufactured by Kanto Chemical Co., Inc.) as a catalyst, and 201 g of alkylnaphthalene (BARREL process oil B-28AN manufactured by MATSUMURA OIL Co., Ltd., boiling point: 430° C.) as a solvent were placed. Then, heating was started, and nitrogen gas (flow rate: 68 NmL/min) and ammonia gas (flow rate: 348 NmL/min) were introduced at 170° C. After further elevating the temperature, bubbling in the reaction solution was started at 270° C., and the temperature was elevated to 300° C. The reaction solution was stirred at 100 rpm for 7 hours to carry out a cyanation reaction.

After the reaction finished, the same operation as in Example 1 was carried out, and analysis by GC was carried out.

The yield of 1,4-dicyanocyclohexane was 91.9 mol %.

Example 9

In a 500 mL five neck flask equipped with a stirring blade, a gas introduction tube, a thermocouple and a dehydration apparatus, 100 g (0.58 mol) of 1,4-cyclohexanedicarboxylic acid, 0.81 g of zinc oxide (manufactured by Kanto Chemical Co., Inc.) as a catalyst, and 201 g of alkylnaphthalene (BARREL process oil B-28AN manufactured by MATSUMURA OIL Co., Ltd., boiling point: 430° C.) as a solvent were placed. Then, heating was started, and nitrogen gas (flow rate: 68 NmL/min) and ammonia gas (flow rate: 348 NmL/min) were introduced at 170° C. After further elevating the temperature, bubbling in the reaction solution was started at 270° C., and the temperature was elevated to 300° C. The reaction solution was stirred at 300 rpm for 5 hours to carry out a cyanation reaction.

After the reaction finished, the same operation as in Example 1 was carried out, and analysis by GC was carried out.

The yield of 1,4-dicyanocyclohexane was 93.1 mol %.

Example 10

In a 500 mL five neck flask equipped with a stirring blade, a gas introduction tube, a thermocouple and a dehydration apparatus, 100 g (0.58 mol) of 1,4-cyclohexanedicarboxylic acid, 0.80 g of zinc oxide (manufactured by Kanto Chemical Co., Inc.) as a catalyst, and 201 g of alkylnaphthalene (BARREL process oil B-28AN manufactured by MATSUMURA OIL Co., Ltd., boiling point: 430° C.) as a solvent were placed. Then, heating was started, and ammonia gas (flow rate: 174 NmL/min) was introduced. After further elevating the temperature, bubbling in the reaction solution was started at 270° C., and the temperature was elevated to 300° C. The reaction solution was stirred at 200 rpm for 9 hours to carry out a cyanation reaction.

After the reaction finished, the same operation as in Example 1 was carried out, and analysis by GC was carried out.

The yield of 1,4-dicyanocyclohexane was 94.1 mol %.

Example 11

In a 500 mL five neck flask equipped with a stirring blade, a gas introduction tube, a thermocouple and a dehydration apparatus, 100 g (0.58 mol) of 1,4-cyclohexanedicarboxylic acid, 0.20 g of zinc oxide (manufactured by Kanto Chemical Co., Inc.) as a catalyst, and 204 g of alkylnaphthalene (BARREL process oil B-28AN manufactured by MATSUMURA OIL Co., Ltd., boiling point: 430° C.) as a solvent were placed. Then, heating was started, and nitrogen gas (flow rate: 68 NmL/min) and ammonia gas (flow rate: 348 NmL/min) were introduced at 170° C. After further elevating the temperature, bubbling in the reaction solution was started at 270° C., and the temperature was elevated to 300° C. The reaction solution was stirred at 200 rpm for 7 hours to carry out a cyanation reaction.

After the reaction finished, the same operation as in Example 1 was carried out, and analysis by GC was carried out.

The yield of 1,4-dicyanocyclohexane was 95.2 mol %.

Example 12

In a 500 mL five neck flask equipped with a stirring blade, a gas introduction tube, a thermocouple and a dehydration apparatus, 100 g (0.58 mol) of 1,4-cyclohexanedicarboxylic acid, 0.40 g of zinc oxide (manufactured by Kanto Chemical Co., Inc.) as a catalyst, and 200 g of alkylnaphthalene (BARREL process oil B-28AN manufactured by MATSUMURA OIL Co., Ltd., boiling point: 430° C.) as a solvent were placed. Then, heating was started, and nitrogen gas (flow rate: 68 NmL/min) and ammonia gas (flow rate: 348 NmL/min) were introduced at 170° C. After further elevating the temperature, bubbling in the reaction solution was started at 270° C., and the temperature was elevated to 300° C. The reaction solution was stirred at 200 rpm for 6 hours to carry out a cyanation reaction.

After the reaction finished, the same operation as in Example 1 was carried out, and analysis by GC was carried out.

The yield of 1,4-dicyanocyclohexane was 93.0 mol %.

Example 13

In a 500 mL five neck flask equipped with a stirring blade, a gas introduction tube, a thermocouple and a dehydration apparatus, 100 g (0.58 mol) of 1,4-cyclohexanedicarboxylic acid, 0.40 g of zinc oxide (manufactured by Kanto Chemical Co., Inc.) as a catalyst, and 200 g of alkylnaphthalene (BARREL process oil B-28AN manufactured by MATSUMURA OIL Co., Ltd., boiling point: 430° C.) as a solvent were placed. Then, heating was started, and nitrogen gas (flow rate: 68 NmL/min) and ammonia gas (flow rate: 348 NmL/min) were introduced at 170° C. After further elevating the temperature, bubbling in the reaction solution was started at 270° C., and the temperature was elevated to 300° C. The reaction solution was stirred at 300 rpm for 7 hours to carry out a cyanation reaction.

After the reaction finished, the same operation as in Example 1 was carried out, and analysis by GC was carried out.

The yield of 1,4-dicyanocyclohexane was 95.5 mol %.

Example 14

In a 500 mL five neck flask equipped with a stirring blade, a gas introduction tube, a thermocouple and a dehydration apparatus, 100 g (0.58 mol) of 1,4-cyclohexanedicarboxylic acid, 1.60 g of zinc oxide (manufactured by Kanto Chemical Co., Inc.) as a catalyst, and 206 g of alkylnaphthalene (BARREL process oil B-28AN manufactured by MATSUMURA OIL Co., Ltd., boiling point: 430° C.) as a solvent were placed. Then, heating was started, and nitrogen gas (flow rate: 68 NmL/min) and ammonia gas (flow rate: 348 NmL/min) were introduced at 170° C. After further elevating the temperature, bubbling in the reaction solution was started at 270° C., and the temperature was elevated to 300° C. The reaction solution was stirred at 200 rpm for 5 hours to carry out a cyanation reaction.

After the reaction finished, the same operation as in Example 1 was carried out, and analysis by GC was carried out.

The yield of 1,4-dicyanocyclohexane was 81.0 mol %.

Example 15

In a 100 mL five neck flask equipped with a stirring blade, a gas introduction tube, a thermocouple and a dehydration apparatus, 12 g (0.06 mol (amount of substance calculated as 1.8 ammonium salt)) of a heated concentrate of an aqueous ammonia solution of 1,4-cyclohexanedicarboxylic acid, 0.24 g of zinc oxide (manufactured by Kanto Chemical Co., Inc.) as a catalyst, and 20 g of alkylnaphthalene (BARREL process oil B-28AN manufactured by MATSUMURA OIL Co., Ltd., boiling point: 430° C.) as a solvent were placed. Then, heating was started, and nitrogen gas (flow rate: 20 mL/min) and ammonia gas (flow rate: 52 mL/min) were introduced at 170° C. After further elevating the temperature, bubbling in the reaction solution was started at 270° C., and the temperature was elevated to 300° C. The reaction solution was stirred at 300 rpm for 3.5 hours to carry out a cyanation reaction.

After the reaction finished, the same operation as in Example 1 was carried out, and analysis by GC was carried out.

The yield of 1,4-dicyanocyclohexane was 85.7 mol %.

The heated concentrate of an aqueous ammonia solution of 1,4-cyclohexanedicarboxylic acid was prepared as follows.

First, 50 g (0.29 mol) of 1,4-cyclohexanedicarboxylic acid, 45 g of 28 mass % ammonia water, and 128 g of water were placed. After distilling off water under reduced pressure, the resultant mixture was dried at 70° C. for 2 hours. When the amount of substance of 1,4-cyclohexanedicarboxylic acid was defined as 1, the ammonia salt was confirmed to be 1.8 moles by elemental analysis.

Comparative Example 1

In a 100 mL five neck flask equipped with a stirring blade, a gas introduction tube, a thermocouple and a dehydration apparatus, 30 g (0.17 mol) of 1,4-cyclohexanedicarboxylic acid, 0.25 g of zinc oxide (manufactured by Kanto Chemical Co., Inc.) as a catalyst, 30.1 g of 1,3-dimethyl-2-imidazolidinone (manufactured by Tokyo Chemical Industry Co., Ltd., boiling point: 220° C.) as a solvent, 23.5 g of 28 mass % ammonia water, and 6.7 g of water were placed. Then, heating was started, and nitrogen gas (flow rate: 20 NmL/min) and ammonia gas (flow rate: 52 NmL/min) were introduced at 170° C. After further elevating the temperature, bubbling in the reaction solution was started at 270° C., and the temperature was elevated to 300° C. The reaction solution was stirred at 300 rpm for 6.5 hours to carry out a cyanation reaction.

After the reaction finished, the same operation as in Example 1 was carried out except that the reaction product was dissolved in methanol instead of tetrahydrofuran, and analysis by GC was carried out.

The yield of 1,4-dicyanocyclohexane was 9.7 mol %.

Comparative Example 2

In a 100 mL five neck flask equipped with a stirring blade, a gas introduction tube, a thermocouple and a dehydration apparatus, 30 g (0.17 mol) of 1,4-cyclohexanedicarboxylic acid, 0.24 g of zinc oxide (manufactured by Kanto Chemical Co., Inc.) as a catalyst, 6.1 g of triethylene glycol (manufactured by Tokyo Chemical Industry Co., Ltd., boiling point: 276° C.) as a solvent, 23.5 g of 28 mass % ammonia water, and 6.7 g of water were placed. Then, heating was started, and nitrogen gas (flow rate: 20 NmL/min) and ammonia gas (flow rate: 52 NmL/min) were introduced at 170° C. After further elevating the temperature, bubbling in the reaction solution was started at 270° C., and the temperature was elevated to 300° C. The reaction solution was stirred at 300 rpm for 6.5 hours to carry out a cyanation reaction.

After the reaction finished, the same operation as in Example 1 was carried out except that the reaction product was dissolved in methanol instead of tetrahydrofuran, and analysis by GC was carried out.

The yield of 1,4-dicyanocyclohexane was 54.6 mol %.

Comparative Example 3

In a 100 mL five neck flask equipped with a stirring blade, a gas introduction tube, a thermocouple and a dehydration apparatus, 10 g (0.06 mol) of 1,4-cyclohexanedicarboxylic acid, 0.24 g of zinc oxide (manufactured by Kanto Chemical Co., Inc.) as a catalyst, and 21 g of n-alkylbenzene (manufactured by Great Orient Chemical (Taicang) Co., Ltd., boiling point: 293.5° C. (distillation temperature: 280 to 307° C.)) as a solvent were placed. Then, heating was started, and nitrogen gas (flow rate: 20 NmL/min) and ammonia gas (flow rate: 52 NmL/min) were introduced at 170° C. After further elevating the temperature, bubbling in the reaction solution was started at 270° C., and the temperature was elevated to 300° C. The reaction solution was stirred at 300 rpm for 3.5 hours to carry out a cyanation reaction.

After the reaction finished, the same operation as in Example 1 was carried out, and analysis by GC was carried out.

The yield of 1,4-dicyanocyclohexane was 51.2 mol %.

Placement, reaction conditions and results for Examples 1 to 4 are shown in Table 1.

Placement, reaction conditions and results for Examples 5 to 9 are shown in Table 2.

Placement, reaction conditions and results for Examples 10 to 14 are shown in Table 3.

Placement, reaction conditions and results for Example 15 are shown in Table 4.

Placement, reaction conditions and results for Comparative Examples 1 to 3 are shown in Table 5.

TABLE 1

|  |  |  | Example 1 | Example 2 | Example 3 | Example 4 |
|---|---|---|---|---|---|---|
| Placement | Reactant | g | 10 | 10 | 10 | 10 |
|  | 1,4-CHDA | mol | 0.06 | 0.06 | 0.06 | 0.06 |
|  | Catalyst | g | 0.24 | 0.24 | 0.24 | 0.24 |
|  | Catalyst/Reactant | wt % | 2.4 | 2.4 | 2.4 | 2.4 |
|  | Solvent | Solvent Name | Alkylnaphthalene | Stearic Acid Amide | Stearonitrile | Triphenylmethane |
|  |  | g | 20 | 20 | 20 | 20 |
|  |  | Boiling Point | 430 | 250-251 (12 Torr) | 274 (13 kPa) | 359 |
| Conditions | $NH_3$ | ml/min | 52 | 52 | 52 | 52 |
|  |  | g/hr | 2.5 | 2.4 | 2.4 | 2.6 |
|  | $NH_3$/Reactant | Molar Ratio/hr | 2.5 | 2.4 | 2.4 | 2.6 |
|  |  | Molar Ratio | 8.6 | 8.4 | 8.6 | 9.2 |
|  | $N_2$ | ml/min | 20 | 20 | 20 | 20 |
|  | Stirring | rpm | 300 | 300 | 300 | 300 |
|  | Temperature | ° C. | 300 | 300 | 300 | 300 |
|  | Time | Temperature Elevation h | 0.4 | 0.9 | 0.5 | 0.7 |
|  |  | Reaction h | 3.5 | 3.5 | 3.5 | 3.5 |
| Results | 1,4-CHDN | mol % | 86.7 | 89.2 | 88.7 | 91.5 |
|  | Proportion of High Boiling Substance to 1,4-CHDN | % | 0.59 | 0.16 | 0.11 | 0.22 |

TABLE 2

|  | Summary |  | Example 5 | Example 6 | Example 7 | Example 8 | Example 9 |
|---|---|---|---|---|---|---|---|
| Placement | Reactant | g | 100 | 100 | 50 | 100 | 100 |
|  | 1,4-CHDA | mol | 0.58 | 0.58 | 0.29 | 0.58 | 0.58 |
|  | Catalyst | g | 0.80 | 0.80 | 0.40 | 0.80 | 0.81 |
|  | Catalyst/Reactant | wt % | 0.80 | 0.80 | 0.80 | 0.80 | 0.81 |
|  | Solvent (Alkylnaphthalene; Boiling Point 430° C.) | g | 200 | 201 | 151 | 201 | 201 |
| Conditions | $NH_3$ | ml/min | 174 | 348 | 174 | 348 | 348 |
|  |  | g/hr | 8.11 | 16.15 | 8.14 | 16.22 | 16.15 |
|  | $NH_3$/Reactant | Molar Ratio/hr | 0.8 | 1.6 | 1.6 | 1.6 | 1.6 |
|  |  | Molar Ratio | 6.6 | 8.2 | 13.1 | 11.5 | 8.2 |
|  | $N_2$ | ml/min | 68 | 68 | 34 | 68 | 68 |
|  | Stirring | rpm | 200 | 200 | 200 | 100 | 300 |
|  | Temperature | ° C. | 300 | 300 | 300 | 300 | 300 |
|  | Time | Temperature Elevation h | 0.6 | 0.7 | 0.6 | 0.9 | 0.8 |
|  |  | Reaction h | 8 | 5 | 8 | 7 | 5 |
| Results | 1,4-CHDN (Total) | mol % | 92.0 | 89.0 | 94.3 | 91.9 | 93.1 |
|  | Proportion of High Boiling Substance to 1,4-CHDN | % | 0.48 | 0.39 | 0.35 | 0.40 | 0.42 |

TABLE 3

| | Summary | | Example 10 | Example 11 | Example 12 | Example 13 | Example 14 |
|---|---|---|---|---|---|---|---|
| Placement | Reactant | g | 100 | 100 | 100 | 100 | 100 |
| | 1,4-CHDA | mol | 0.58 | 0.58 | 0.58 | 0.58 | 0.58 |
| | Catalyst | g | 0.80 | 0.20 | 0.40 | 0.40 | 1.60 |
| | Catalyst/Reactant | wt % | 0.80 | 0.20 | 0.40 | 0.40 | 1.60 |
| | Solvent (Alkylnaphthalene; Boiling Point 430° C.) | g | 201 | 204 | 200 | 200 | 206 |
| Conditions | NH$_3$ | ml/min | 174 | 348 | 348 | 348 | 346 |
| | | g/hr | 8.11 | 16.28 | 14.29 | 15.91 | 16.16 |
| | NH$_3$/Reactant | Molar Ratio/hr | 0.8 | 1.6 | 1.4 | 1.6 | 1.6 |
| | | Molar Ratio | 7.4 | 11.5 | 8.7 | 11.3 | 8.2 |
| | N$_2$ | ml/min | 0 | 68 | 68 | 68 | 68 |
| | Stirring | rpm | 200 | 200 | 200 | 300 | 200 |
| | Temperature | ° C. | 300 | 300 | 300 | 300 | 300 |
| | Time | Temperature Elevation h | 0.8 | 0.9 | 0.9 | 0.8 | 0.9 |
| | | Reaction h | 9 | 7 | 6 | 7 | 5 |
| Results | 1,4-CHDN (Total) | mol % | 94.1 | 95.2 | 93.0 | 95.5 | 81.0 |
| | Proportion of High Boiling Substance to 1,4-CHDN | % | 0.43 | 0.42 | 0.48 | 0.50 | 0.49 |

TABLE 4

| | | | Example 15 |
|---|---|---|---|
| Placement | Heated Concentrate of 1,4-CHDA Aqueous Ammonia Solution | g | 12 |
| | | mol (Calculated as 1.8 Ammonium Salt) | 0.06 |
| | Catalyst | g | 0.24 |
| | Catalyst/Reactant | wt % | 2.0 |
| | Solvent | Solvent Name | Alkylnaphthalene |
| | | g | 20 |
| | | Boiling Point | 430 |
| Conditions | NH$_3$ | ml/min | 52 |
| | | g/hr | 2.6 |
| | NH$_3$/Reactant | Molar Ratio/hr | 2.5 |
| | | Molar Ratio | 8.9 |
| | N$_2$ | ml/min | 20 |
| | Stirring | rpm | 300 |
| | Temperature | ° C. | 300 |
| | Time | Temperature Elevation h | 0.6 |
| | | Reaction h | 3.5 |
| Results | 1,4-CHDN | mol % | 85.7 |
| | Proportion of High Boiling Substance to 1,4-CHDN | % | 0.39 |

TABLE 5

| | | | Comparative Example 1 | Comparative Example 2 | Comparative Example 3 |
|---|---|---|---|---|---|
| Placement | Reactant | g | 30 | 30 | 10 |
| | 1,4-CHDA | mol | 0.17 | 0.17 | 0.06 |
| | Catalyst | g | 0.25 | 0.24 | 0.24 |
| | Catalyst/Reactant | wt % | 0.8 | 0.8 | 2.4 |
| | Solvent | Solvent Name | 1,3-DMI | Triethylene Glycol | n-Alkylbenzene |
| | | g | 30.1 | 6.1 | 21 |
| | | Boiling Point ° C. | 220 | 276 | 280-307 |
| | Ammonia Water | g | 23.5 | 23.4 | 0 |
| | Water | g | 6.7 | 6.8 | 0 |
| Conditions | NH$_3$ | ml/min | 52 | 52 | 52 |
| | | g/hr | 2.4 | 2.4 | 2.6 |
| | NH$_3$/Reactant | Molar Ratio/hr | 0.8 | 0.8 | 2.6 |
| | | Molar Ratio | 5.3 | 5.2 | 9.1 |
| | N$_2$ | ml/min | 20 | 20 | 20 |
| | Stirring | rpm | 300 | 300 | 300 |
| | Temperature | ° C. | 300 | 300 | 300 |
| | Time | Temperature Elevation h | | | 0.5 |
| | | Reaction h | 6.5 | 6.5 | 3.5 |
| Results | 1,4-CHDN | mol % | 9.7 | 54.6 | 51.2 |
| | Proportion of High Boiling Substance to 1,4-CHDN | % | N/A | N/A | 0.76 |

In these Tables, the high boiling substance was an impurity having a structure in which dicyanocyclohexane trimerizes to form a triazine ring. The proportion of the high boiling substance to 1,4-dicyanocyclohexane was a value (%) obtained by calculating a value by dividing the mol % of the high boiling substance (a compound in which dicyanocyclohexane trimerizes to form a triazine ring) by the mol % of 1,4-CHDN and multiplying the obtained value by 100.

N/A indicates that measurement was not carried out.

This application is based on Japanese Patent Application No. 2017-158153 filed on Aug. 18, 2017, the contents of which are incorporated herein by reference.

INDUSTRIAL APPLICABILITY

The present invention can provide a production method for dicyanocyclohexane by which dicyanocyclohexane is obtained with a high yield and generation of impurities can be suppressed, and it has industrial applicability as a raw material of an epoxy curing agent, polyamide, polyurethane and the like.

The invention claimed is:

1. A method for producing dicyanocyclohexane, the method comprising:
reacting cyclohexanedicarboxylic acid and/or a salt thereof, or a heated concentrate of an aqueous ammonia solution of cyclohexanedicarboxylic acid with ammonia in a solvent having a boiling point equal to or higher than a reaction temperature, thereby producing dicyanocyclohexane,
wherein the boiling point of the solvent having the boiling point equal to or higher than the reaction temperature is 350° C. or higher.

2. The method according to claim 1, further comprising: conducting a hydrogenation reaction of phthalic acid in an aqueous ammonia solution, thereby producing the cyclohexanedicarboxylic acid and/or the salt thereof, or the aqueous ammonia solution of cyclohexanedicarboxylic acid.

3. The method according to claim 2,
wherein a part of an aqueous ammonia solution included in a reaction solution after the conducting is used as an ammonia source for the reacting.

4. The method according to claim 1, further comprising:
heating the aqueous ammonia solution of cyclohexanedicarboxylic acid to 100 to 200° C. to remove at least a part of water, thereby forming the heated concentrate.

5. A method for producing dicyanocyclohexane, the method comprising:
reacting cyclohexanedicarboxylic acid and/or a salt thereof, or a heated concentrate of an aqueous ammonia solution of cyclohexanedicarboxylic acid with ammonia in a solvent having a boiling point equal to or higher than a reaction temperature, thereby producing dicyanocyclohexane,
wherein the solvent having the boiling point equal to or higher than the reaction temperature is one or more selected from the group consisting of alkylnaphthalene, stearic acid amide, stearonitrile and triphenylmethane.

6. A method for producing bis(aminomethyl)cyclohexane, the method comprising:
obtaining dicyanocyclohexane by the method according to claim 1, and
obtaining bis(aminomethyl)cyclohexane by subjecting the dicyanocyclohexane to a hydrogenation reaction.

7. The method according to claim 2, further comprising:
heating the aqueous ammonia solution of cyclohexanedicarboxylic acid to 100 to 200° C. to remove at least a part of water, thereby forming the heated concentrate.

8. The method according to claim 3, further comprising:
heating the aqueous ammonia solution of cyclohexanedicarboxylic acid to 100 to 200° C. to remove at least a part of water, thereby forming the heated concentrate.

9. A method for producing bis(aminomethyl)cyclohexane, the method comprising:
obtaining dicyanocyclohexane by the method according to claim 2, and
obtaining bis(aminomethyl)cyclohexane by subjecting the dicyanocyclohexane to a hydrogenation reaction.

10. A method for producing bis(aminomethyl)cyclohexane, the method comprising:
obtaining dicyanocyclohexane by the method according to claim 3, and
obtaining bis(aminomethyl)cyclohexane by subjecting the dicyanocyclohexane to a hydrogenation reaction.

11. A method for producing bis(aminomethyl)cyclohexane, the method comprising:
obtaining dicyanocyclohexane by the method according to claim 4, and
obtaining bis(aminomethyl)cyclohexane by subjecting the dicyanocyclohexane to a hydrogenation reaction.

12. A method for producing bis(aminomethyl)cyclohexane, the method comprising:
obtaining dicyanocyclohexane by the method according to claim 5, and
obtaining bis(aminomethyl)cyclohexane by subjecting the dicyanocyclohexane to a hydrogenation reaction.

13. A method for producing bis(aminomethyl)cyclohexane, the method comprising:
obtaining dicyanocyclohexane by the method according to claim 7, and
obtaining bis(aminomethyl)cyclohexane by subjecting the dicyanocyclohexane to a hydrogenation reaction.

14. A method for producing bis(aminomethyl)cyclohexane, the method comprising:
obtaining dicyanocyclohexane by the method according to claim 8, and
obtaining bis(aminomethyl)cyclohexane by subjecting the dicyanocyclohexane to a hydrogenation reaction.

15. The method according to claim 1, wherein the boiling point of the solvent having the boiling point equal to or higher than the reaction temperature is higher than 350° C.

16. The method according to claim 1, wherein the boiling point of the solvent having the boiling point equal to or higher than the reaction temperature is higher than 350° C. to 600° C. or lower.

* * * * *